United States Patent [19]

Heistand, II

[11] Patent Number: 4,761,491
[45] Date of Patent: Aug. 2, 1988

[54] PREPARATION OF 2-SUBSTITUTED-1,3-DIOXACYCLOALKANES FROM DIOLS AND DIUNSATURATED ETHERS

[75] Inventor: Robert H. Heistand, II, East Walpole, Mass.

[73] Assignee: The Dow Chemical Company, Midland, Mich.

[21] Appl. No.: 920,633

[22] Filed: Oct. 20, 1986

Related U.S. Application Data

[63] Continuation of Ser. No. 686,068, Dec. 24, 1984, abandoned.

[51] Int. Cl.$^4$ .................. C07D 317/20; C07D 317/48
[52] U.S. Cl. ..................................... 549/435; 549/430; 549/434; 549/436; 549/437; 549/448
[58] Field of Search ............... 549/434, 435, 436, 437, 549/448, 430

[56] References Cited

U.S. PATENT DOCUMENTS

| | | | |
|---|---|---|---|
| 3,969,416 | 7/1976 | Shaw | 549/437 |
| 4,118,400 | 10/1978 | Michaely | 549/434 |
| 4,155,915 | 5/1979 | Arndt et al. | 549/434 |
| 4,252,738 | 2/1981 | Hartmann et al. | 549/437 |
| 4,450,276 | 5/1984 | Gehlhaus et al. | 549/435 |
| 4,540,800 | 9/1985 | Inaba et al. | 549/437 |

*Primary Examiner*—Nicky Chan
*Attorney, Agent, or Firm*—M. F. Zuckerman

[57] ABSTRACT

2-Substituted-1,3-dioxacycloalkanes (also known as acetonides) (such as

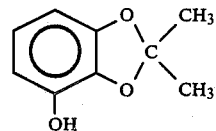

(4-hydroxy-2,2-dimethyl-1,3-benzodioxole)) are prepared by reacting a diol (such as 1,2,3-trihydroxybenzene) and a diunsaturated ether (such as diisopropenyl ether). The reaction is exothermic and produces a ketone as the only by-product. The invention has utility in hydroxyl moiety "protection" and in pesticide synthesis.

17 Claims, No Drawings

PREPARATION OF 2-SUBSTITUTED-1,3-DIOXACYCLOALKANES FROM DIOLS AND DIUNSATURATED ETHERS

CROSS-REFERENCE TO RELATED APPLICATION

This is a continuation of application Ser. No. 686,068, filed Dec. 24, 1984, now abandoned.

BACKGROUND OF THE INVENTION

This invention relates to the preparation of 2-substituted-1,3-dioxacycloalkanes, also known as "acetonides". In particular, this invention relates to such a process wherein the reactants are a diol and a diunsaturated ether.

2-Substituted-1,3-dioxacycloalkanes, hereinafter referred to as DOCA's, are useful in a number of respects.

In the synthesis of many organic compounds, a diol compound must undergo certain reactions without "damaging" the alcohol moieties. If these reactions would cause damage to the alcohol moieties, a typical approach is to first "block" or "protect" the hydroxyls by reacting them with a group which is inert in the reaction that can damage bare hydroxyls, but which can be easily removed, yielding the hydroxyl functionality, at a later time. When the compound to be protected has at least 2 hydroxyl moieties, the formation of a DOCA is an excellent method of protecting the compound.

Further, in the manufacture of certain compounds, such as pesticides, a DOCA moiety is an important part of the final compound.

DOCA compounds and their syntheses are not unknown. Typical synthesis routes employ a diol and a second reagent, and may also require a catalyst, heat, pressure, or other reaction conditions.

Larson and Hernandez, *J. Org. Chem.*, Vol. 38, No. 22, p. 3935 (1973), disclose a method where unsaturated trimethylsiloxy compounds are reacted with diols to yield DOCA's in a mildly exothermic reaction. This reference claims yields of 70 to 80 percent. The principal by-product is trimethylsilanol.

Ball, *Biochemical Preparation*, published by John Wiley & Sons, pp. 31-34 (1952), is representative of many references which teach the formation of DOCA's with alkanones (ketones) such as propanone (acetone), in the presence of a catalyst such as $ZnCl_2$.

Debost, Gelas, and Horton, *J. Org. Chem.*, Vol. 48, p. 1381 (1983), teach the formation of DOCA's with 2-alkoxypropenes. This has a small positive free energy, but its main disadvantage is the production of an alcohol as a by-product. This creates the need for special purification steps, especially since most end uses of DOCA's require that they be neat or in an aprotic solvent, rather than a protic solvent such as an alcohol.

U.S. Pat. No. 4,067,883 teaches the formation of DOCA's from aromatic diols and a compound of the formula

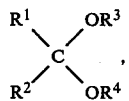

with the application of heat. This also produces alcohol by-products.

Accordingly, there is a need for a process to prepare DOCA's which is both energy efffficient (i.e., has a high positive free energy), and has minimal by-product formation (especially the absence of protic by-products).

SUMMARY OF THE INVENTION

Briefly, the invention is a process for making a DOCA by reacting a diol with a diunsaturated ether under conditions sufficient to form a DOCA. The reaction may optionally take place with the aid of an aprotic solvent and an acid catalyst. The process of the invention has very favorable thermodynamics and has the advantage of producing a ketone as the only significant by-product.

DETAILED DESCRIPTION OF THE INVENTION

In this specification and claims, numerical ranges are not critical unless otherwise stated. That is, the numerical ranges may be read as if they were prefaced with the word "about" or "substantially".

As the diol, virtually any compound having a plurality of hydroxyl moieties, and sterically capable of forming a ring with only a single additional carbon atom, may be used. Generally, there will be from 2 to 5, desirably 2 to 4, preferably 2 or 3, and most preferably 2, atoms separating the hydroxyl moieties of the diol.

The diol may be either aromatic or aliphatic, and may contain multiple fused or unfused rings. Structures having fused rings are preferable when there are more than two atoms separating the hydroxyl moieties.

The diol may contain more than 2 hydroxyl moieties (e.g., D-manitol and 1,2,3-trihydroxybenzene), and may contain other moieties, either as an integral part of the molecular chain of the diol, or as a substituent moiety. Atoms which may be part of the molecular chain include N, S, and O. Moieties which may be present as substituents include $=O$, $=S$, $—C=O$, $—NR^1R^2$, and so forth. Of course, the above exemplified atoms and moieties are not an exhaustive list, but are merely meant to be illustrative. Exemplary classes of diol compounds include 6-membered rings (either aromatic or non-aromatic) having at least two adjacent hydroxyl moieties; and carbohydrates or analogous compounds which represent reduced carbohydrates (this is not to require that the carbohydrate actually be capable of being reduced, but only that the analogous compound be the theoretical reduced equivalent). Specific exemplary compounds are included in the examples.

As the diunsaturated ether, the compound must be of the formula

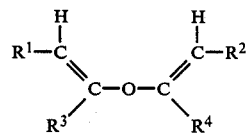

wherein each of $R^1$ and $R^2$ are independently a hydrogen atom or an inert organic moiety that will not hinder the reaction desirably hydrogen or unsubstituted hydrocarbon moieties, more desirably hydrogen or unsubstituted $C_1$ to $C_{12}$ moieties, preferably hydrogen or unsubstituted $C_1$ to $C_6$ moieties, more preferably hydrogen or unsubstituted $C_1$ to $C_3$ moieties, and most preferably hydrogen; and each of $R^3$ and $R^4$ are indepenently an inert organic moiety that will not hinder the reaction, desirably unsubstituted hydrocarbon moieties, more desirably unsubstituted $C_1$ to $C_{12}$ moieties, preferably unsubstituted $C_1$ to $C_6$ moieties, more preferably $C_1$ to $C_3$ moieties, and most preferably methyl moieties. By the term "inert organic moiety" is meant an organic moiety which may be substituted, but which does not contain moieties which will interfere with the reaction with the diol. The preferred species is (bis)1-methylethenyl ether (also known as diisopropenyl) ether):

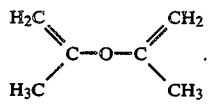

These compounds and their syntheses are well-known to those skilled in the art. For example, diisopropenyl ether can be prepared by dehydrohalogenation of $\beta,\beta^1$-dichlorodiisopropyl ether (see, for example, GB No. 1,004,809).

The molar ratio of diunsaturated ether to diol may be any ratio that will permit the formation of the desired DOCA product, but is desirably 0.5:1 to 2:1, preferably 1:1 to 1.5:1. Excess diunsaturated ether can lead to multiple additions if the diol has multiple sites available for reaction.

The reactants may be combined under a variety of conditions. If the reactants are liquid, they may be blended and reacted neat. If they are solids, they may be melted or dissolved in a solvent. Preferably, the reactants are dissolved in a solvent. Because most end uses of DOCA's require further reaction in an aprotic solvent, it is greatly preferred that the solvent for the reaction of the instant invention be aprotic. Indeed, if a protic solvent is used, one of the advantages of the invention, the absence of a protic solvent by-product, is diminished. Preferred classes of solvents include halocarbons, ethers, ketones, and amides. Specific preferred solvents include tetrahydrofuran, acetone, and dimethylsulfoxide. The solvent to diol mass ratio may be any ratio that will permit the formation of the desired DOCA product, but is desirably from 0:1 to 1000:1, but is preferably 0:1 to 10:1.

Reaction temperature and pressure may vary in a range sufficient to produce DOCA's, but are conveniently near ambient conditions. The temperature is desirably 0° C. to 150° C., preferably 10° C. to 100° C., more preferably 20° C. to 60° C. Because the reaction is exothermic, the temperature of the reaction mass will generally be above ambient temperature. Cooling means may be used, but for small reactions are not generally necessary. Reaction pressure is not critical, but is desirably 100 to 400 kPa, preferably about 100 kPa.

The time of reaction may vary, and like the temperature and pressure, is not critical. The reaction time is desirably 0.25 to 3 hours, preferably 0.5 to 2 hours, and more preferably 1 to 1.5 hours.

Although not essential, the use of a catalyst is greatly preferred. Generally, the catalyst will be an acid catalyst, preferably a Bronsted or Lewis acid. Trifluoroacetic acid is a preferred species. The acid catalyst may be in the form of a strong acid ion-exchange resin. The molar ratios of catalyst to diol are desirably 0 to 1:1, preferably $10^{-4}$:1 to $10^{-2}$:1.

The reactants, catalyst and solvent may be combined all at once, or may be added to the reaction vessel over a period of time. It is generally convenient to add all of the solvent, diol, and catalyst at the beginning, and to then add the diunsaturated ether over a period of time.

When the reaction is complete, solvent removal, if desired, may be accomplished by means such as distillation or crystallization of the product. Because the only by-product is a ketone (e.g., acetone if diisopropenyl ether is used as a reactant), solvent removal is particularly easy. However, because ketones are aprotic solvents, their removal is not usually necessary. If the product is isolated from the solvent, it may be further purified by sublimation or crystallization and washings.

The following examples are presented to further illustrate the invention. In the examples, no effort was made to determine if the color of products was due to the product itself, or to impurities contained therein.

EXAMPLE 1

Preparation of 4-hydroxy-2,2-dimethyl-1,3-benzodioxole (pyrogallol-1,2-acetonide)

To a stirred, ambient temperature solution of 12.61 g (0.100 mole) of 1,2,3-trihydroxybenzene (pyrogallol) and 12.00 g (0.122 mole) of diisopropenyl ether in 40 ml of dry tetrahydrofuran, 5 μl ($6.5 \times 10^{-5}$ mole) of $CF_3COOH$ was added. After 30 minutes, 2.0 ml ($1.6 \times 10^{-2}$ mole) of diisopropenyl ether was added, followed 10 minutes later by 3 μl ($3.9 \times 10^{-5}$ mole) of $CF_3COOH$. After an additional 30 minutes, another 2 ml ($1.6 \times 10^{-2}$ mole) of diisopropenyl ether was added. The reaction was stirred for an additional 30 minutes, and the solvent was stripped under reduced pressure. Sublimation of the crude product at 60° C. and 0.08 mm Hg (0.01 kPa) for 10 hours yielded 15.62 g ($9.4 \times 10^{-2}$ mole, 94 percent) of a white crystaline product having a meltinig point of 88° C. to 90° C. Nuclear magnetic resonance and mass spectrum analysis confirmed the structure to be:

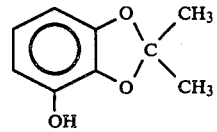

EXAMPLE 2

Preparation of 5-hydroxy-2,2-dimethyl-1,3-benzodioxole (1,2,4-trihydroxybenzene-1,2-acetonide)

To a stirred, ambient temperature solution of 8.99 g ($7.13 \times 10^{-2}$ mole) of 1,2,4-trihydroxybenzene and 6.94 g ($7.08 \times 10^{-2}$ mole) of diisopropenyl ether in 31 ml of dry tetrahydrofuran, 5 μl ($6.5 \times 10^{-5}$ mole) of $CF_3COOH$ was added. After 17 minutes, 2.0 ml ($1.6 \times 10^{-2}$ mole) of diisopropenyl ether and 3 μl ($3.9 \times 10^{-5}$ mole) of $CF_3COOH$ were added. After an additional 18 minutes, a second 2.0 ml ($1.6 \times 10^{-2}$ mole) of diisopropenyl ether was added. The reaction was stirred for another 20 minutes and the solvent removed under reduced pressure. Vacuum distillation with a short path still at 0.07 mm Hg (0.009 kPa) produced 5.92 g (boiling point 87° C. to 99° C., 98 percent product, 0.4 percent 1,2,4-trihydroxybenzene) and 2.31 g (boiling point 99° C. to 101° C., 92 percent product, 5.2 percent 1,2,4-trihydroxybenzene) of a light yellow oil. The yield was 70 percent ($4.96 \times 10^{-2}$ mole). Nuclear magnetic resonance and mass spectrum analysis confirmed the structure to be:

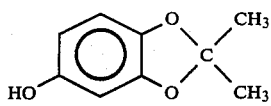

EXAMPLE 3

Preparation of
2,2-dimethyl-5-(2-propenyloxy)-1,3-benzodioxole (Compound A) and
2,2-di-(5-oxo-2,2-dimethyl-1,3-benzodioxole)-propane (Compound B)

Six microliters ($7.8 \times 10^{-5}$ mole) of $CF_3COOH$ were added to a stirred solution of 9.02 g ($7.15 \times 10^{-2}$ mole) of 1,2,4-trihydroxybenzene and 5.3 ml ($4.3 \times 10^{-2}$ mole) of diisopropenyl ether in 30 ml of acetone. The exothermic reaction reached a low reflux. After 27 minutes, 5.6 ml ($4.5 \times 10^{-2}$ mole) of diisopropenyl ether and 6 μl ($7.8 \times 10^{-5}$ mole) of $CF_3COOH$ were added causing the solution to reflux again. Additional amounts of 4.2 ml ($3.4 \times 10^{-2}$ mole) diisopropenyl ether and 3.0 μl ($3.9 \times 10^{-5}$ mole) of acid, 4.4 ml ($3.6 \times 10^{-2}$ mole) of diisopropenyl ether and 3 μl ($3.9 \times 10^{-5}$ mole) of acid, and 4.0 ml ($3.2 \times 10^{-2}$ mole) of diisopropenyl ether and 4.0 μl ($5.2 \times 10^{-5}$ mole) of acid were added after intervals of 74, 85 and 40 minutes respectively. The solvent was removed under reduced pressure 40 minutes after the last addition. Vacuum distillation at 0.19 mm Hg (0.025 kPa) produced two fractions: boiling point 75° C. to 79° C., 9.03 g, pale beige liquid, 94 percent compound A; boiling point 79° C. to 84° C., 3.54 g, pale yellow very viscous oil which crystallized upon standing, 17 percent compound A and 74 percent compound B. Combined yield of compounds A and B based on 1,2,4-trihydroxybenzene is 82 percent; molar ratio is 6.1:1, A to B respectively. Nuclear magnetic resonance and mass spectrum analysis demonstrated that the structure of compound A is:

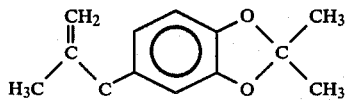

and that the structure of compound B is:

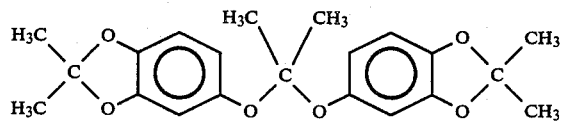

EXAMPLE 4

Preparation of 5-formyl-2,2-dimethyl-1,3-benzodioxole (protocatechualdehyde acetonide Method A:

A solution of 13.6 ml (0.110 mole) of diisopropenyl ether in 10 ml of acetone was added dropwise over a period of 42 minutes to a stirred suspension of 14.98 g (0.180 mole) of 3,4-dihydroxybenzaldehyde (protocatechualdehyde) and 6 μl ($7.8 \times 10^{-5}$ mole) of $CF_3COOH$ in 40 ml of acetone. After 50 minutes, 5 μl ($6.5 \times 10^{-5}$ mole) of $CF_3COOH$ was added; 34 minutes later the solution was homogeneous. After another 56 minutes, 3.0 ml ($2.4 \times 10^{-2}$ mole) of diisopropenyl ether and 6 μl ($7.8 \times 10^{-5}$ mole) of $CF_3COOH$ were added; another 3 ml of diisopropenyl ether and 6 μl of acid were added after another hour. The solvent was evaporated under reduced pressure after an additional 75 minutes of reaction time. The dark viscous crude was vacuum distilled at 0.23 mm Hg (0.032 kPa) in a short path still. After the collection of a purple forerun, 14.69 g ($8.25 \times 10^{-3}$ mole, 97 percent product) of a pale blue liquid was collected. Overnight the liquid turned the color of burgundy wine, but no changes occurred in gas chromatograph analysis. The product had a boiling point of 81° C. to 84° C. and was obtained in 76 percent yield.

Method B:

In 90 ml of acetone 31.00 g (0.244 mole) of sublimed 3,4-dihydroxybenzaldehyde (protocatechualdehyde) was slurried with 25 ml (0.203 mole) of diisopropenyl ether. After mixing for 14 minutes, 10 μl ($1.3 \times 10^{-4}$ mole) of $CF_3COOH$ was added followed 31 minutes later by 5 μl ($6.5 \times 10^{-5}$ mole) of $CF_3COOH$. The solution became homogeneous 35 minutes later. Two additions of 7 ml ($5.7 \times 10^{-2}$ mole) of diisopropenyl ether with 6 μl ($7.8 \times 10^{-5}$ mole) of $CF_3COOH$ and 7 ml ($5.7 \times 10^{-2}$ mole) of diisopropenyl ether with 10 μl ($1.3 \times 10^{-4}$ mole) of $CF_3COOH$ were added after periods of 25 and 35 minutes had elapsed, respectively. One hour after the last addition, the solvent was evaporated and the crude oil vacuum distilled at 0.84 mm Hg (0.112 kPa). A forerun of 0.93 g (>97 percent product, boiling point 90° C., dark blue, which changes to yellow green), a fraction of 19.16 g (>98.6 percent product, boiling point 91° C. to 93° C., pale blue which changes to yellow green and finally burgundy) and a fraction of 8.61 g (>97 percent product, boiling point 93° C. to 95° C., colorless but changes to blue and then orange/pink overnight) were collected to yield 0.161 mole (72 percent) of product. Nuclear magnetic resonance and mass spectrum analysis demonstrated the product of both methods to have the structure:

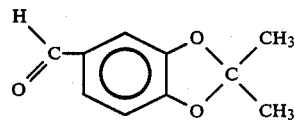

EXAMPLE 5

Preparation of
trans-hexahydro-2,2-dimethyl-1,3-benzodioxole (trans-1,2-cyclohexanediol acetonide Three microliters ($3.9 \times 10^{-5}$ mole) of $CF_3COOH$ was added to trans-1,2-cyclohexanediol (2.88 g, $2.48 \times 10^{-2}$ mole) and diisopropenyl ether (2.0 ml, $1.62 \times 10^{-2}$ mole) dissolved in 25 ml of acetone at 50° C. After 11 minutes, 0.5 ml ($4.05 \times 10^{-3}$ mole) of diisopenpenyl ether and 3 μl ($3.9 \times 10^{-5}$ mole) of $CF_3COOH$ were added, followed 15 minutes later by 0.5 ml ($4.05 \times 10^{-3}$ mole) of diisopropenyl ether. The reaction was completed after another hour of stirring, and the solvent evaporated under reduced pressure. The crude liquid was chilled and filtered to remove 0.32 g ($2.75 \times 10^{-3}$ mole) of starting diol. Vacuum distillation at 21-24 mm Hg (2.8-3.2 kPa) in the presence of diphenyl ether as a high boiling solvent produced 1.93 g (92 percent product and 7.2 percent diphenyl ether; boiling point 84° C. to 85° C.) and 0.31 g (77 percent product and 22 percent diphenyl ether; boiling point 88° C. to 90° C.) of colorless liquid. The yield was $1.29 \times 10^{-2}$ mole (52 percent). The product has a boiling point of 92° C. to 96° C. at 22 mm Hg (2.9 kPa). Nuclear magnetic resonance and mass spectrum analysis showed the product to have the structure:

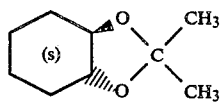

Example 6

Preparation of 1,2:5,6-di-O-isopropylidene-D-mannitol (D-mannitol-1,2,5,6-diacetonide)

Five microliters ($6.5 \times 10^{-5}$ mole) of $CF_3COOH$ were added to a solution of 7.41 g ($4.07 \times 10^{-2}$ mole) of D-mannitol and 8.0 ml ($6.48 \times 10^{-2}$ mole) of diisopropenyl ether in 50 ml of heated dimethylsulfoxide at a constant temperature of 65° C. After 70 minutes, 1.5 ml ($1.22 \times 10^{-2}$ mole) of diisopropenyl ether was added. Forty-seven minutes later, the dimethylsulfoxide was evaporated at 18 mm Hg (2.4 kPa) and elevated temperature to reduce the volume of 10 ml. The viscous crude contained 83 percent product, 3.0 percent triacetonide and 9 percent monoacetonide. With the aid of acetone, the crude was transferred to a petri dish for further evaporation of the solvents. White needles crystallized overnight. Vacuum filtration collected 4.28 g ($1.63 \times 10^{-2}$ mole, 40 percent yield) of the product. The filtrate contained D-mannitol from hydrolysis of the product. The product had a melting point of 116° C. to 117° C. Nuclear magnetic resonance and mass spectrum analysis demonstrated that the structure was:

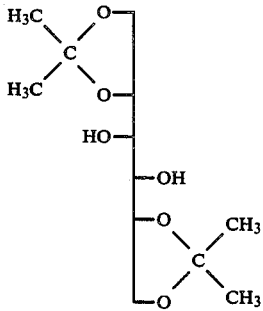

What is claimed is:

1. A method of preparing a 2-substituted-1,3-dioxacycloalkane and a by-product consisting of a ketone comprising reacting together:
    (a) a diol selected from the group consisting of aliphatic compounds having a plurality of hydroxyl moieties and aromatic compounds having a plurality of hydroxyl moieties such that there are two carbon atoms separating the hydroxyl moieties, and such that said diol is capable of forming a ring with a single additional carbon atom; and
    (b) a diunsaturated ether of the formula:

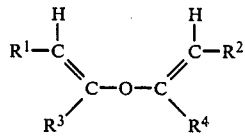

wherein each of $R^1$ and $R^2$ are independently a hydrogen atom or an inert organic moiety selected from the group consisting of unsubstituted $C^1$ to $C^{12}$ hydrocarbon moieties and substituted organic moieties that will not hinder the reaction; and wherein each of $R^3$ and $R^4$ are independently an inert organic moiety selected from the group consisting of unsubstituted $C^1$ to $C^{12}$ hydrocarbon moieties and substituted organic moieties that will not hinder the reaction;

wherein said diol and said diunsaturated ether are reacted under conditions sufficient to form said 2-substituted-1,3-dioxacycloalkane and said ketone.

2. The method of claim 1 wherein (a) and (b) are reacted together in the presence of an acid catalyst.
3. The method of claim 2 wherein the catalyst is a Bronsted or Lewis acid.
4. The method of claim 1 wherein (a) and (b) are reacted together in the presence of a solvent.
5. The method of claim 4 wherein the solvent is an aprotic solvent.
6. The method of claim 1 wherein the diol comprises a 6-membered ring having at least two adjacent hydroxyl moieties.
7. The method of claim 6 wherein the ring is aromatic.
8. The method of claim 1 wherein the diol is a carbohydrate or an analogous compound representing a reduced carbohydrate.
9. The method of claim 1 wherein $R^1$ and $R^2$ are hydrogens.
10. The method of claim 9 wherein $R^3$ and $R^4$ are methyl moieties.
11. The method of claim 1 wherein the diunsaturated ether is reacted in excess.
12. The method of claim 3 wherein the acid catalyst comprises trifluoroacetic acid.
13. The method of claim 7 wherein the diol comprises 1,2,3- or 1,2,4-trihydroxybenzene.
14. A method of preparing a 2-substituted-1,3-dioxacycloalkane and a ketone by-product comprising reacting together:
    (a) an organic compound having a plurality of hydroxyl moieties which are separated by two carbon atoms, the organic compound being sterically capable of forming a ring with a single additional carbon atom; and
    (b) a diunsaturated ether of the formula

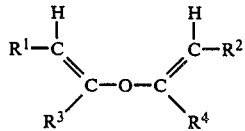

wherein each of $R^1$ and $R^2$ are independently a hydrogen atom or an inert organic moiety that will not hinder the reaction; and each of $R^3$ and $R^4$ are independently an inert organic moiety that will not hinder the reaction;

wherein said organic compound having a plurality of hydroxyl moieties and said diunsaturated ether are reacted under conditions sufficient to form said 2-substituted-1,3-dioxacycloalkane and said ketone.

15. The method of claim 14 wherein the 2-substituted-1,3-dioxacycloalkane is 1,2,3- or 1,2,4-trihydroxybenzene-1,2-acetonide; the organic compound is 1,2,3- or 1,2,4-trihydroxybenzene; and the diunsaturated ether is diisopropenyl ether.

16. A method of preparing a 2-substituted-1,3- dioxacycloalkane selected from the group consisting of:

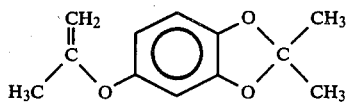 (A)

and

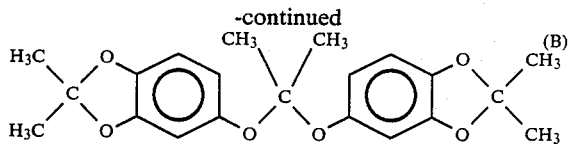

and a by-product consisting of a ketone comprising reacting together:
(a) 1,2,4-trihydroxybenzene, and
(b) diisopropenyl ether
wherein said diol and an excess of said diunsaturated ether are reacted under conditions sufficient to form said 2-substituted-1,3-dioxacycloalkane and said ketone.

17. A method of preparing a 2-substituted-1,3-dioxacycloalkane having the structure:

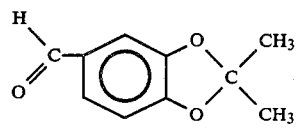

and a ketone by-product comprising reacting together (a) 3,4-dihydroxybenzaldehyde and (b) diisopropenyl ether, under conditions sufficient to form said 2-substituted-1,3-dioxacycloalkane and said ketone.

* * * * *